United States Patent [19]

Weissman

[11] 4,337,043
[45] Jun. 29, 1982

[54] DENTAL ANCHOR

[75] Inventor: Bernard Weissman, New York, N.Y.

[73] Assignee: IPCO Corporation, White Plains, N.Y.

[21] Appl. No.: 845,628

[22] Filed: Oct. 26, 1977

[51] Int. Cl.³ .............................................. A61C 5/04
[52] U.S. Cl. ................................................... 433/225
[58] Field of Search .............. 32/15, 6, 7, 10 A, 10 R; 433/8, 16, 225

[56] References Cited

U.S. PATENT DOCUMENTS

| 2,413,333 | 12/1946 | Myerson | 433/195 |
| 3,499,222 | 3/1970 | Linkow et al. | 32/10 A |
| 3,928,915 | 12/1975 | Ellman | 32/15 |

FOREIGN PATENT DOCUMENTS

| 905714 | 7/1972 | Canada | 32/7 |
| 1081887 | 6/1967 | United Kingdom | 408/215 |
| 1389218 | 4/1975 | United Kingdom | 408/215 |

Primary Examiner—Gene Mancene
Assistant Examiner—John J. Wilson
Attorney, Agent, or Firm—Friedman, Goodman & Teitelbaum

[57] ABSTRACT

A dental anchor is disclosed comprising an elongated body member for insertion into a channel in a tooth in order to anchor a superstructure to the tooth. The body member has at least one section with a substantially square cross-section. The longitudinal corner portions of the section are provided with self tapping threads for threading into the channel. Preferably, the body member includes two similar sections joined together by a reduced thickness portion so that one section can be bent relative to the other section when seated in the channel to provide an anchoring portion for the superstructure. Two dental anchors may be joined together by a reduced thickness frangible member, where the thickness of the reduced thickness portion of each dental anchor has a thickness greater than any thickness of the frangible member. Accordingly, the longitudinal side surfaces of the dental anchor are spaced from the walls of the channel when the anchor is seated in the channel to provide spaces therebetween, so that cement can be disposed in these spaces to fixedly secure the dental anchor in the channel.

6 Claims, 5 Drawing Figures

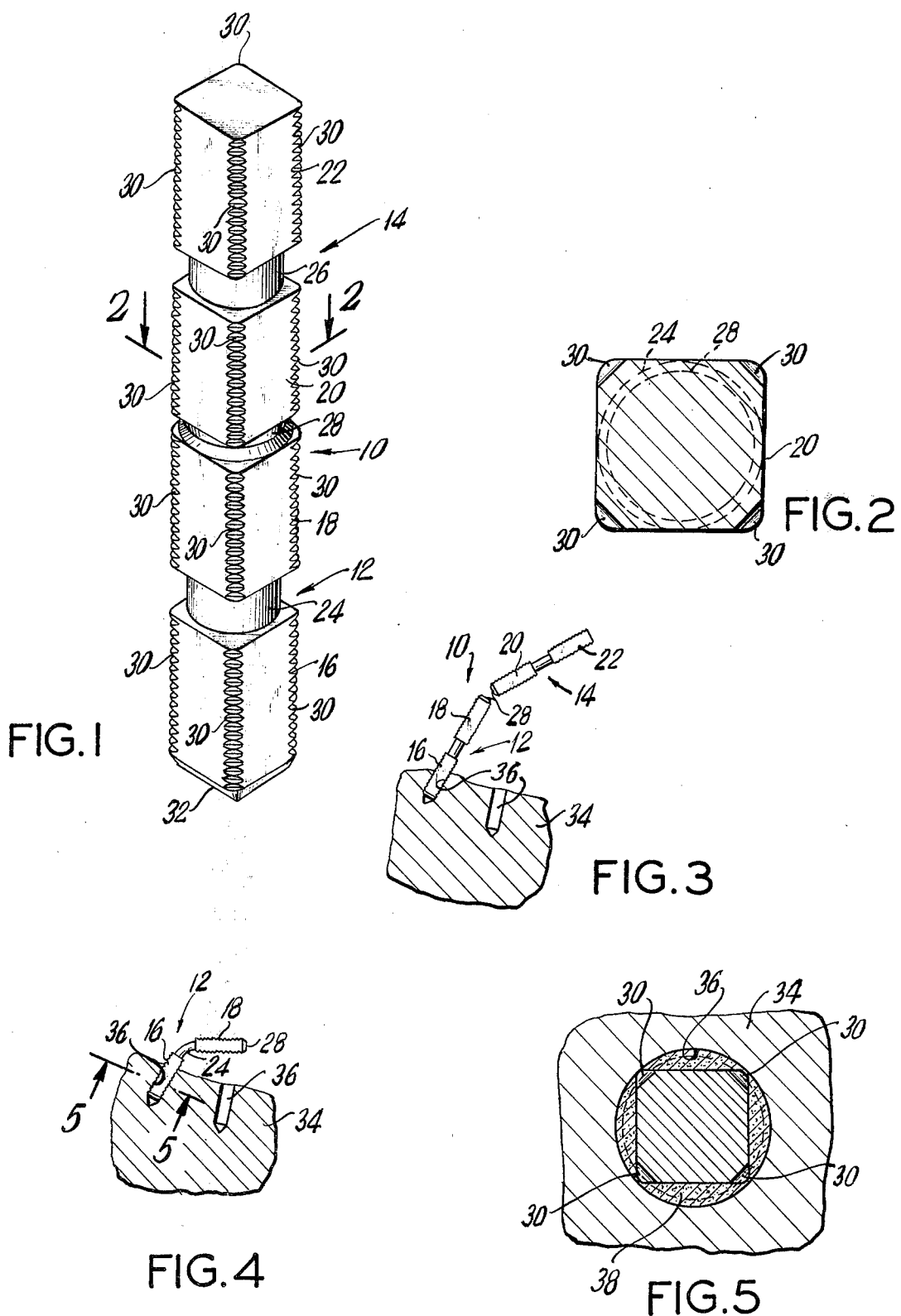

DENTAL ANCHOR

BACKGROUND OF THE INVENTION

The present invention relates to dentistry in general, and more particularly to an improved dental anchor for building superstructures on broken or undermined dentition.

Anchoring a superstructure to the understructure of a tooth usually requires drilling a number of channels into the tooth or understructure. Depending upon the tooth involved, one or more anchoring rods are then secured in the channels and are allowed to protrude above the understructure with the exposed or protruding portions of the rods serving to anchor the superstructure. It should be noted, that in this type of dental operation, these rods are extremely small, for example, being on the order of 0.03" in diameter and approximately 0.20" in length.

The rods are retained in the channels by (1) cementation, by (2) being screwed into the channels, or by (3) friction lock where the rod is forced into a channel of smaller diameter. According to tensile tests performed on rods secured in dentin, self-threading rods have the greatest retention of the three types tested, where the friction lock is classified as intermediate, and the cemented rod is the least retentive.

It is noted, that prior art dental anchors are disclosed in my U.S. Pat. No. 3,434,209 showing a structure of a single dental anchor, and my U.S. Pat. No. 3,675,328 showing two dental anchors interconnected to one another which are readily severable from one another.

It is noted, that stresses are normally present when inserting the prior art dental anchors into the channels. Additionally, the construction of the prior art dental anchors require torque for insertion thereof into the channels provided in the tooth.

SUMMARY OF THE INVENTION

Accordingly, it is an object of the present invention to provide an improved dental anchor for building a superstructure on broken or undermined dentition.

Another object of the present invention is to provide an improved dental anchor which is fixedly secured in the understructure of a tooth.

A further object of the present invention is to provide an improved dental anchor which reduced the stresses normally present when inserting the prior art dental anchors into the channels provided in the understructure of a tooth, which also reduces the torque required during this insertion.

Still another object of the present invention is to provide a dental anchor in the form of sections with substantially square cross-sections, where self tapping threads are provided along the longitudinal corner portions of the sections.

Yet another object of the present invention is to provide an improved dental anchor as set forth above, wherein the longitudinal side surfaces of the dental anchor are spaced from the walls of the channel when the anchor is seated therein to provide spaces therebetween, so that cement can be disposed in these spaces to fixedly secure the dental anchor in the channel.

These objects are achieved in accordance with a preferred embodiment of the present invention, wherein the dental anchor comprises an elongated body member having at least one section with a substantially square cross-section, the longitudinal corner portions of the section being provided with self tapping threads for threading into the channel. The body member includes two similar sections joined together by a reduced thickness portion so that one section can be bent relative to the other section. Preferably, two dental anchors are joined together by a reduced thickness frangible member having a thickness less than the thickness of the above mentioned reduced thickness portions of each dental anchor. When the anchor is seated in the channel, the longitudinal side surfaces of the dental anchor are spaced from the walls of the channel to provide spaces therebetween to receive cement therein to fixedly secure the dental anchor in the channel.

BRIEF DESCRIPTION OF THE DRAWINGS

With the above and additional objects and advantages in view, as will hereinafter appear, this invention comprises the devices, combinations and arrangements of parts hereinafter described by way of example and illustrated in the accompanying drawings of a preferred embodiment in which:

FIG. 1 is a perspective view illustrating the dental anchor comprising the present invention;

FIG. 2 is a transverse sectional view taken along line 2—2 of FIG. 1;

FIG. 3 is a cross-sectional view of a tooth or dentition with its surface excavated prior to building of a superstructure thereon, showing the first dental anchor inserted therein;

FIG. 4 is a cross-sectional view similar to FIG. 3 illustrating a bent dental anchor therein; and FIG. 5 is a cross-sectional view taken along line 5—5 of FIG. 4.

DETAILED DESCRIPTION OF THE PREFERRED EMBODIMENT

Referring now to the drawing, FIG. 1 shows a dental anchor 10 of the present invention comprising two reinforcing or anchor rods 12, 14 interconnected to one another. However it is understood, that the present invention relates just as well to the construction of a single reinforcing or anchor rod and also to the construction of a dental anchor having more than two reinforcing or anchor rods interconnected to one another.

Each of the anchor rods 12, 14 includes first and second coaxial sections 16, 18 and 20, 22 which are joined together by intermediate reduced thickness portions 24 and 26. Additionally, section 18 of anchor rod 12 is joined to the section 20 of anchor rod 14 by a frangible reduced thickness portion 28 to define a one piece elongated dental anchor 10. The dimension of the reduced thickness portion 28 is selected such that it has a cross-sectional thickness less than that of the intermediate portions 24, 26 in order that the elongated body of the dental anchor 10 will fracture at this reduced thickness portion 28 after being inserted into a channel formed in the understructure of a tooth or dentition, in a manner as set forth in my above-mentioned patents to whhich reference may be made.

As shown in FIGS. 1 and 2, each of the sections 16, 18, 20, 22 has a substantially square cross-section to provide each section with four longitudinal side surfaces joined by four longitudinal corner portions, where the intermediate portions 24, 26 are cylindrical. Additonally, the sections 16, 18, 20, 22 are provided with self tapping screw threads 30, however such threads 30 are only located along the longitudinal corner portions thereof. Preferably, at least one or all of the sections 16, 18, 20 and 22 has at least one end thereof terminating in a bevelled or chamfered end 32.

Referring to FIGS. 3, 4 and 5, the tooth 34 is prepared for building a super-structure thereon in the manner set forth in my above-mentioned patents, where a plurality of channels 36 having predetermined diameters are drilled therein. The dental anchors are now inserted into the channels 36, where the diagonals of the square cross-section of each anchor is greater than the diameter of each channel. The dental anchor can be rotated either by a manual tool or a power tool attached to the end section 22. The opposite end section 16 is thus threaded into the channel 36 by application of a slight downward pressure and simultaneous rotation of the dental anchor 10 as set forth above. Thus the threads 30 are self tapped into the tooth and form complementary threads in the walls of the channel to threadably engage the dental anchor.

It is noted, that the construction of this dental anchor having the threads only at its corners, reduces the stresses normally present when inserting the prior art dental anchors into the channels. Additionally, the construction of the dental anchor of the present invention reduces the torque required for the insertion thereof into the channels provided in the tooth. Furthermore, it is noted that section 22 can also be provided with a chamfered end. Accordingly, either section 16 or 22 can be initially threaded into the channel, where both ends of the anchor can have the same configuration.

Once the section 16 of the anchor 10 is seated in the channel 36 of the tooth 34, further rotation of the anchor will cause the frangible reduced portion 28 to break off, where the intermediate portion 24 and the rear section 18 will now protrude from the tooth as shown in the drawings. The anchor rod 14 is now ready to be threaded into a second channel 36 in the tooth in the same manner as mentioned above.

As shown in FIG. 4, the protruding section 18 is bent or inclined relative to the inserted section 16 to provide an anchoring portion for the superstructure, where the bending takes place along the intermediate portion 24 which has a reduced cross-section for this purpose. However, before the bending thereof, it is preferable to provide commercially available cement 38 or the like, which is well known in the art, into the channel 36. The cement 38 can be coated onto the section 16, can be inserted into the channel 36 before the insertion of the section 16, or can be applied after the insertion of the section 16, depending upon the requirements thereof.

It is noted, that the cement 38 functions to (1) seal the channel 36, (2) fixes the anchor section 16 in the channel 36, (3) prevents the anchor section 16 from turning or rotating after the cement has hardened, and (4) facilitates the bending of the dental rod by securing the dental end section 16 to the tooth 34.

Numerous alterations of the structure herein disclosed will suggest themselves to those skilled in the art. However, it is to be understood that the present disclosure relates to a preferred embodiment of the invention which is for purposes of illustration only and is not to be construed as a limitation of the invention.

What is claimed is:

1. A dental anchor for insertion into a channel in a tooth, said dental anchor comprising an elongated body member, said body member having a first section with a substantially square cross-section to provide four longitudinal side surfaces joined by four longitudinal corner portions, each of said corner portions being provided with thread means for self tapping said one section into the channel when said body member is rotated about its longitudinal axis, said longitudinal side surfaces of said first section being spaced from walls of the channel when said first section is being threaded into the channel to reduce self tapping stresses, said body member having a second section along said longitudinal axis, a reduced thickness portion disposed intermediate said first section and second section to permit said second section to be bent relative to said first section after said first section is seated in the channel to provide an anchoring portion for a superstructure, said reduced thickness portion being cylindrical; and said dental anchor further including a second elongated body member along said longitudinal axis, said second body member having a third section with a substantially square cross-section to provide another four longitudinal side surfaces joined by another four longitudinal corner portions, each of said another corner portions being provided with second thread means for self tapping said third section into a second channel when said second body member is rotated about said longitudinal axis, said another four longitudinal side surfaces of said third section being spaced from walls of the second channel when said third section is being threaded into the second channel to reduce self tapping stresses, and a frangible reduced thickness member connecting said second and third sections of said body members together, said reduced thickness cylindrical portion having a thickness greater than any thickness of said frangible reduced thickness member.

2. A dental anchor according to claim 1, wherein said second section has a substantially square cross-section to provide four additional side surfaces joined by four additional corner portions.

3. A dental anchor according to claim 2, wherein said four additional corner portions are each provided with self tapping thread means.

4. A dental anchor according to claim 1, where said second body member includes a fourth section along said longitudinal axis and a second reduced thickness portion disposed intermediate said third and fourth sections to permit said fourth section to be bent relative to said third section after said third section is seated in the second channel to provide another anchoring portion for the superstructure, said second reduced thickness portion being cylindrical.

5. A dental anchor according to claim 4, wherein each said second and fourth sections has a substantially square cross-section to provide four additional side surfaces joined by four additional corner portions on each of said body members.

6. A dental anchor according to claim 5, wherein said four additional corner portions on each of said second and fourth sections are each provided with self tapping thread means.

* * * * *